United States Patent
Camus et al.

(10) Patent No.: US 7,302,286 B2
(45) Date of Patent: Nov. 27, 2007

(54) METHOD AND APPARATUS FOR THE THREE-DIMENSIONAL PRESENTATION OF AN EXAMINATION REGION OF A PATIENT IN THE FORM OF A 3D RECONSTRUCTION IMAGE

(75) Inventors: Estelle Camus, Erlangen (DE); Hendrik Ditt, Hoechstadt (DE); Reinmar Killmann, Forchheim (DE); Norbert Rahn, Forchheim (DE); Siegfried Wach, Hoechstact (DE)

(73) Assignee: Siemens Aktiengesellschaft, Munich (DE)

( * ) Notice: Subject to any disclaimer, the term of this patent is extended or adjusted under 35 U.S.C. 154(b) by 813 days.

(21) Appl. No.: 10/385,865

(22) Filed: Mar. 11, 2003

(65) Prior Publication Data
US 2003/0199748 A1 Oct. 23, 2003

(30) Foreign Application Priority Data
Mar. 11, 2002 (DE) ............... 102 10 650

(51) Int. Cl.
*A61B 5/05* (2006.01)

(52) U.S. Cl. ............ 600/407; 600/424; 600/410; 600/437

(58) Field of Classification Search ........ 382/128, 382/154, 254; 345/653, 654, 679, 680; 600/437, 443, 440, 424, 407, 410; 351/205
See application file for complete search history.

(56) References Cited

U.S. PATENT DOCUMENTS

| 4,945,914 | A | * | 8/1990 | Allen | 600/426 |
| 4,991,579 | A | * | 2/1991 | Allen | 600/426 |
| 5,005,578 | A | * | 4/1991 | Greer et al. | 600/414 |
| 5,016,642 | A | * | 5/1991 | Dukes et al. | 600/509 |
| 5,526,812 | A | * | 6/1996 | Dumoulin et al. | 600/407 |
| 5,787,889 | A | * | 8/1998 | Edwards et al. | 600/443 |
| 6,216,029 | B1 | * | 4/2001 | Paltieli | 600/427 |
| 6,228,028 | B1 | * | 5/2001 | Klein et al. | 600/437 |
| 6,246,898 | B1 | * | 6/2001 | Vesely et al. | 600/424 |
| 6,263,093 | B1 | * | 7/2001 | Mochizuki | 382/128 |
| 6,285,902 | B1 | * | 9/2001 | Kienzle et al. | 600/427 |
| 6,317,621 | B1 | * | 11/2001 | Graumann et al. | 600/424 |
| 6,379,302 | B1 | * | 4/2002 | Kessman et al. | 600/437 |
| 6,572,547 | B2 | * | 6/2003 | Miller et al. | 600/437 |
| 6,652,460 | B2 | * | 11/2003 | Pellegretti et al. | 600/443 |
| 6,669,635 | B2 | * | 12/2003 | Kessman et al. | 600/437 |
| 6,768,496 | B2 | * | 7/2004 | Bieger et al. | 345/630 |
| 6,968,224 | B2 | * | 11/2005 | Kessman et al. | 600/407 |
| 2001/0035871 | A1 | * | 11/2001 | Bieger et al. | 345/630 |
| 2003/0097068 | A1 | * | 5/2003 | Hossack et al. | 600/443 |

(Continued)

FOREIGN PATENT DOCUMENTS

WO     WO 98/38908     9/1998

*Primary Examiner*—Brian L. Casler
*Assistant Examiner*—Joel Lamprecht
(74) *Attorney, Agent, or Firm*—Schiff Hardin LLP

(57) ABSTRACT

In a method and apparatus for the three-dimensional presentation of an examination region of a patient in the form of a 3D reconstruction image, a preoperatively acquired 3D image dataset of the examination region is employed in a medical procedure, datasets representing a number of 2D ultrasound images of the examination region are acquired, the preoperative 3D image dataset is updated using the datasets representing 2D ultrasound images, and the 3D reconstruction image is generated on the basis of the updated 3D image dataset.

32 Claims, 2 Drawing Sheets

U.S. PATENT DOCUMENTS

2003/0117393 A1* 6/2003 Sauer et al. ................. 345/419
2003/0220561 A1* 11/2003 Camus et al. ............... 600/424
2004/0059217 A1* 3/2004 Kessman et al. ........... 600/424

* cited by examiner

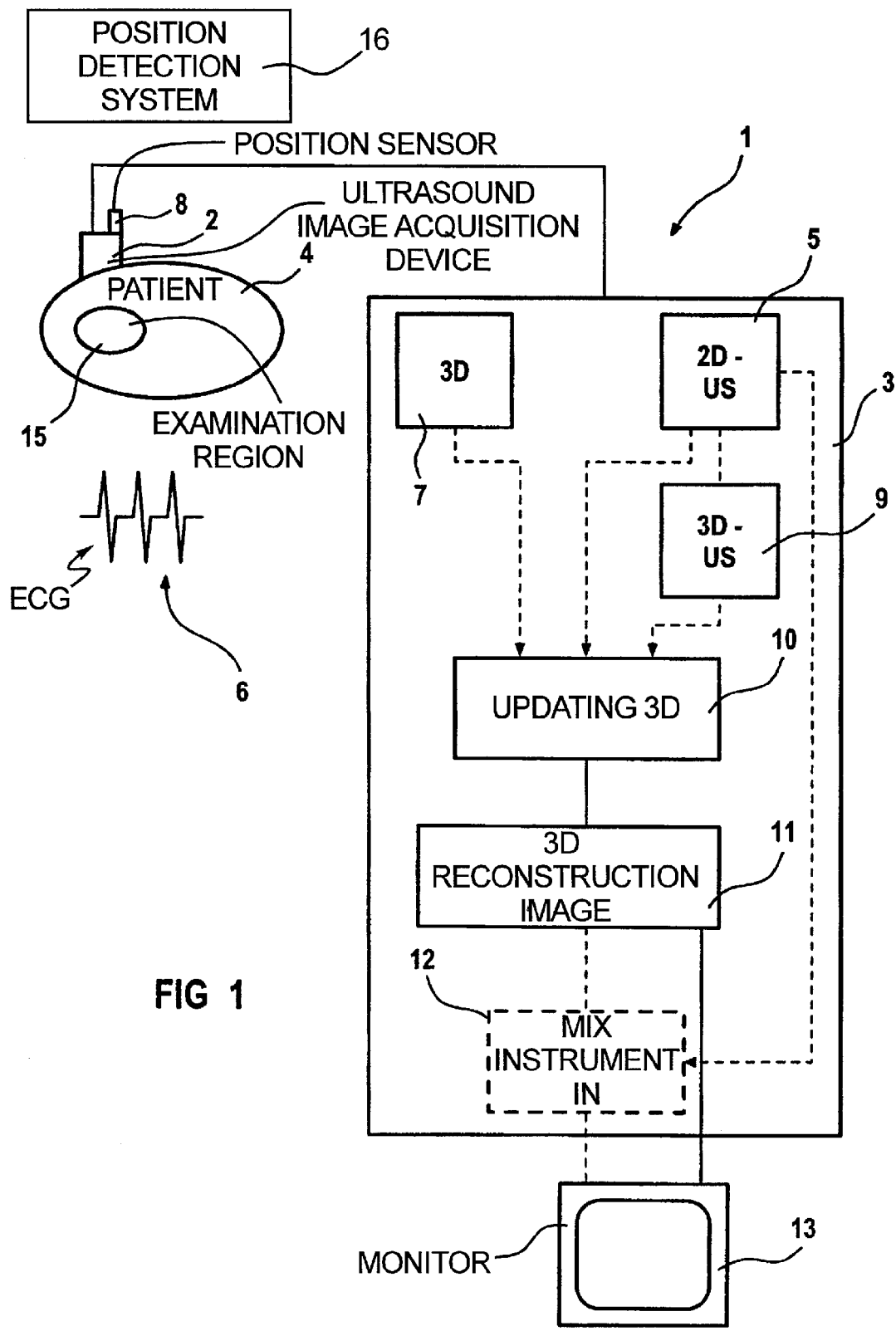

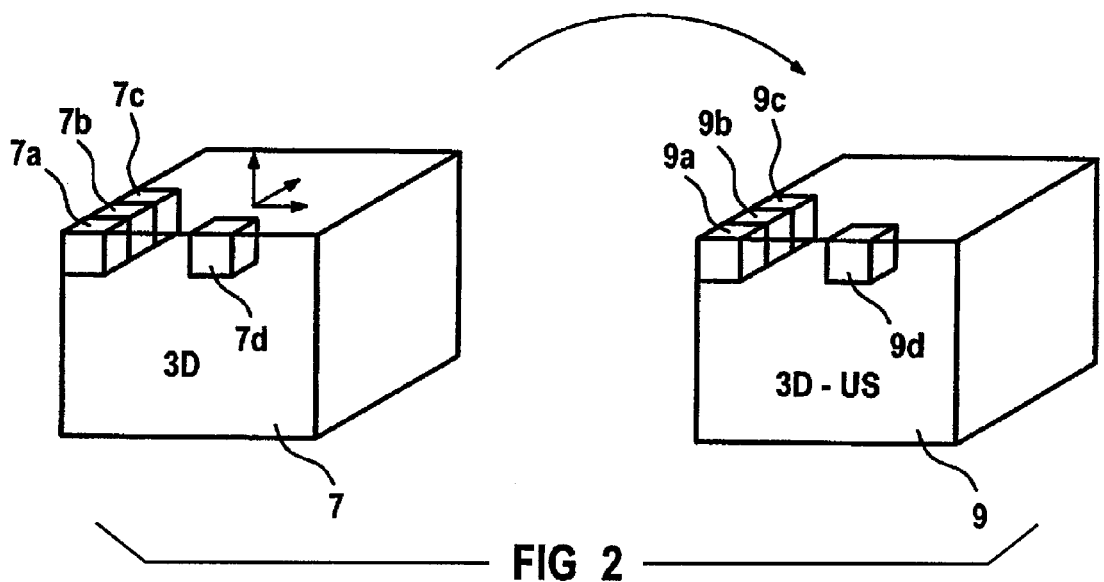
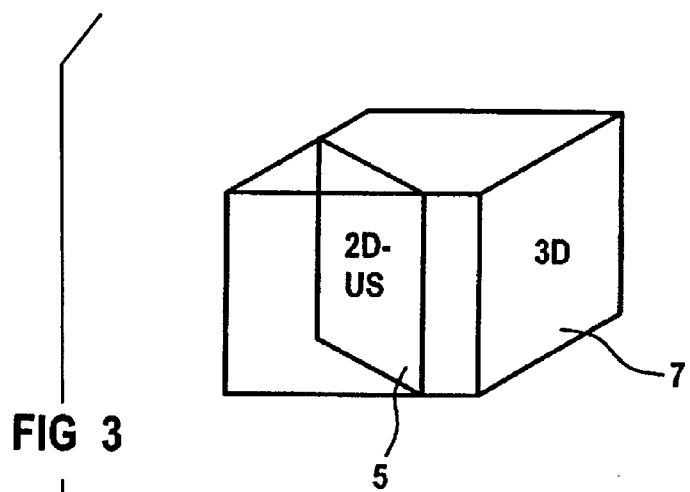
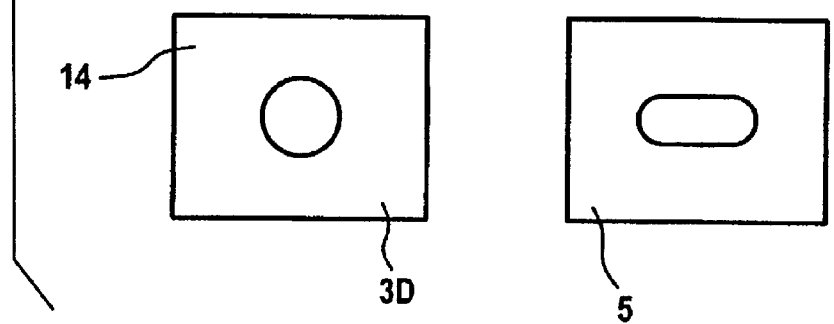

METHOD AND APPARATUS FOR THE THREE-DIMENSIONAL PRESENTATION OF AN EXAMINATION REGION OF A PATIENT IN THE FORM OF A 3D RECONSTRUCTION IMAGE

BACKGROUND OF THE INVENTION

1. Field of the Invention

The present invention is directed to a method and apparatus for the three-dimensional presentation of an examination region of a patient in the form of a 3D reconstruction image.

2. Description of the Prior Art

The three-dimensional presentation of an examination region of a patient in the form of a 3D reconstruction image is becoming increasingly important in the framework of medical examinations or treatments. Examples are minimally invasive treatments using endoscopes, laparoscopes or catheters that are respectively introduced into the examination region of the patient via a small body opening. On the basis of the 3D reconstruction image, the physician is provided with a three-dimensional view of the examination region, for example of the heart, which is useful to the physician for the navigation of the medical instrument. Such 3D reconstruction images, however, also are useful in instances wherein no instrument is to be introduced and only a presentation that serves for diagnostic purposes is required.

Preoperatively acquired 3D image datasets, i.e. datasets that were acquired an arbitrary time before the actual examination or treatment, often are employed for the reconstruction of a 3D reconstruction image. Particularly when the 3D reconstruction image is employed in the context of ongoing intervention, difficulties can occur due to anatomical conditions that have changed since the preoperative exposure, i.e. the 3D reconstruction image that is reconstructed based on the preoperative image data no longer represents the current anatomical or positional conditions. For example, the patient may have gained or lost weight, can lie in a different position on the patient bed, etc. Ambiguities arise therefrom for the attending physician that can make the diagnosis, examination or treatment more difficult, particularly the intervention treatment.

SUMMARY OF THE INVENTION

An object of the present invention is to provide a method and apparatus for the three-dimensional presentation of an examination region of a patient in the form of a 3D reconstruction image, wherein the aforementioned disadvantages are alleviated.

This object is achieved in accordance with the invention in a method and apparatus wherein a preoperatively acquired 3D image dataset of the examination region is employed in a medical procedure, 2D datasets of a number of 2D ultrasound images of the examination region are acquired, the preoperative 3D image dataset is updated using the datasets of the 2D ultrasound images, and a 3D reconstruction image is generated on the basis of the updated 3D image dataset.

Thus in accordance with the invention the preoperative 3D image dataset is updated at the time of the procedure (examination or treatment or intervention), so that the 3D reconstruction image subsequently reconstructed on the basis of the updated 3D image dataset reproduces the actual anatomical or positional situation. A number of 2D ultrasound images of the examination region are acquired for this purpose. These show the examination region in its current position. The 2D ultrasound images form the basis for the updating. The ultrasound image acquisition is advantageous from a number of points of view. First, it can ensue without great apparatus outlay; second, no radiation stressing of the patient whatsoever occurs due to the ultrasound acquisition. The images also can be acquired very quickly in the context of the ongoing examination or treatment or intervention, so that an excessively longer time for the overall procedure does not occur.

The preoperative 3D image dataset can have been acquired with an arbitrary acquisition modality; it can, thus, be a CT dataset or an MR dataset or a 3D X-ray angiography dataset. All of these datasets allow an exact reconstruction of the examination region. These different datasets also can be updated using image data acquired with a different examination modality, namely an ultrasound device.

In a first embodiment of the invention, the updating of the preoperative 3D image dataset ensues directly on the basis of the 2D ultrasound images. In an alternative version a 3D ultrasound image dataset is reconstructed on the basis of the 2D ultrasound images, and the updating ensues on the basis of this 3D ultrasound image dataset. A combined updating mode is also possible, i.e. the updating can ensue both on the basis of the 2D ultrasound images as well as on the basis of the reconstructed 3D ultrasound image dataset.

When, for example, the updating ensues on the basis of a 3D ultrasound image dataset, then the 3D image dataset and the 3D ultrasound image dataset can be overlaid on one another in accordance with the invention, and those dataset parts of the 3D image dataset that do not adequately agree with the corresponding parts of the 3D ultrasound image dataset are deformed by translation and/or rotation until an adequate superimposition has been achieved. A conforming technique known as "deformable matching" between the preoperative 3D image dataset and the reconstructed 3D ultrasound image dataset is used. A registration is undertaken that deforms the preoperatively acquired image dataset such that it matches the current image dataset better, which should ensue in as short a time as possible in order to keep the waiting time for the patient as short as possible. For this reason, a rigid matching first ensues between the preoperative 3D image dataset and the quasi intraoperatively acquired 3D ultrasound image dataset (the ultrasound volume). No further registration, i.e. modification or deformation of the dataset, is required in the regions wherein the datasets agree well. Only those regions are reconsidered wherein the datasets do not yet coincide to an adequate extent. The two datasets, thus, are subdivided and every inadequately registered region is registered again. To this end, for example, it is possible to produce a 3D reconstruction image and a 3D ultrasound reconstruction image from each dataset and to subdivide the respective, reconstructed volumes into individual voxels of the same size and to then separately compare these voxels to one another. Only those voxels that are not adequately registered relative to one another, i.e. that do not coincide well enough, are registered again. When an adequate registration has been found for each sub-region of the two datasets, these registrations must still be linked to or operated with one another. As a result of this linkage or operation, it is possible that overlaps or gaps may arise. In order to compensate these, in accordance with the invention the overlap or gap regions within the 3D image dataset generated due to the translational and/or rotational deformation are smoothed by interpolation. The time required for the registration can be considerably shortened since a deformation occurs only once at the end given such a registration process and the sub-regions of the datasets are otherwise only rigidly registered.

The determination of the deformation parameters required for the updating of a voxel ensues, for example, by means of a grayscale analysis of the data parts or voxels to be compared. The arrangement relative to one another of the image parts to be compared can be recognized from this grayscale distribution analysis. The actual modification of the image dataset, i.e. the actual updating or deformation, thus ensues when the deformation parameters have been found.

For the updating given direct employment of the 2D ultrasound images, in accordance with the invention, the 2D ultrasound images are acquired with an ultrasound exposure device having a position sensor that supplies information about the spatial orientation and position of the acquired 2D ultrasound image, this ultrasound image being registered with respect to the coordinates of the 3D image dataset, so that the spatial position and orientation of the acquired 2D ultrasound image relative to the 3D image dataset is known. The acquired 2D ultrasound image is mixed with exact position and orientation into a corresponding sectional plane image of the 3D image dataset, which is subsequently deformed corresponding to the 2D ultrasound image. Thus the 2D ultrasound images are directly employed for the updating. The aforementioned position sensor can be integrated into the ultrasound head or applicator. The position and orientation of the position sensor are identified via a suitable position acquisition system in a coordinate system associated with the position acquisition system. This coordinate system and thus the position sensor, is registered (brought into registration with) with the coordinates of the preoperative 3D image dataset, so that the position and orientation of every 2D ultrasound image acquired during the image acquisition is known relative to the preoperative 3D image dataset. The current 2D ultrasound image can be mixed in the preoperative 3D image dataset at the appropriate position with the position and orientation obtained by the position sensor, i.e. it is mixed with exact position and orientation into the corresponding sectional plane image of the 3D image dataset. For the registration and thus updating of the 3D image dataset, a deformation and matching of the 3D image dataset now ensues by deforming the displayed surfaces and contours of the sectional plane image of the 3D image dataset until they correspond to the anatomy shown in the 2D ultrasound image that has been mixed in, i.e., surfaces or geometrical structures are matched.

An improvement of the registration can be achieved by segmenting a surface of the examination region, for example the heart surface, shown in the 3D image dataset before the mixing, and the 2D ultrasound image dataset is subsequently mixed in. As a result of the segmenting, a three-dimensional envelope figure is obtained that shows the surface of the examination region, for example of the heart. By this means, the 2D ultrasound image is subsequently placed with exact orientation and planarity, and the direction in which the 3D surface envelope is to be deformed so that it matches the illustrated 2D contour of the heart in the respective image plane is subsequently determined for defining the deformation parameters. How the deformation should appear for a surface fit is calculated for the determination of the deformation parameters. The actual updating or deformation of the preoperative 3D image dataset subsequently ensues using the deformation parameters. By means of the clear demarcation of the heart surface in the ultrasound image, it is thus possible to determine the spacing and the direction of the same surface in the ultrasound image from the surface in the preoperatively acquired 3D image dataset and, based thereon, to define or modify the deformation parameters in a suitable way.

If the examination region is a rhythmically or arrhythmically moving region, for example the heart, then for an exact presentation the image data from the 3D image dataset to be updated and the acquired 2D ultrasound images must each show the examination region in the same motion phase. In order to enable this, in accordance with the invention the motion phase of a rhythmically or arrhythmically moving examination region is acquired, and only image data from the 3D image dataset that are acquired in the same motion phase as the 2D ultrasound images are employed for the 3D reconstruction. The acquisition of the motion phase is required in the acquisition of the 3D image dataset as well as in the 2D ultrasound image acquisition in order to be able to produce isophase images or volumes. The image data to be updated and thus the reconstruction volume, are expediently based on the phase in which the 2D ultrasound images are acquired. It can also be expedient when, in addition to the motion phase, the respective points in time of the acquisition of the 2D ultrasound images is acquired, and only image data from the 3D image dataset that are also acquired at the same points in time as the 2D ultrasound images are employed for the updating and reconstruction of the 3D reconstruction image.

When the examination is the heart, then an ECG is expediently recorded for acquiring the motion phase and, if used, the time, the acquisition of the 2D ultrasound images being triggered dependent thereon. An ECG likewise is allocated to the image data for the production of the 3D reconstruction image when they are acquired.

The 2D ultrasound images can be acquired extra-corporeally using a known ultrasound exposure device externally applied to the patient. An intracorporeal ultrasound image acquisition is also possible, using a suitable medical instrument, for example in the form of a catheter with an ultrasound exposure head integrated at its tip.

On the basis of the updated 3D image dataset, it is now possible to produce a 3D reconstruction image corresponding to the current anatomical situation. As described, this can be employed for diagnostic purposes; however, it is also possible to use this in the context of an intervention. To this end, for example, the ultrasound images are acquired using an instrument that already has been introduced into the examination region in the context of the interventional procedure, for example a catheter introduced into the heart, and the position of the instrument is determined on the basis of at least one 2D ultrasound image and is displayed in the current 3D reconstruction image. This affords the possibility of online visualization of the catheter with exact position and orientation in the updated 3D reconstruction image. To this end, the 2D ultrasound images that show the catheter can be employed. As an alternative, there is the possibility, for example, of employing and mixing in 2D fluoroscopic images that are acquired with a suitable X-ray device. In this case, a 2D/3D registration or a 2D/3D fusion of the 2D real-time images that show the image of the instrument with the updated, preoperative 3D image dataset must be implemented. When, alternatively, a position sensor is integrated in the catheter, positions and orientation of the instrument can be continuously acquired during the intervention with the assistance of this position sensor and can be mixed into the updated preoperative 3D image dataset. A 3D/3D registration of the coordinates of the position sensor with the coordinates of the updated 3D image dataset is assumed for this purpose. The registration can ensue on the basis of any known 2D/3D or 3D/3D registration methods. Such registration modes are well known to those skilled in the art so a more detailed description is not required.

DESCRIPTION OF THE DRAWINGS

FIG. 1 is a schematic illustration of a medical examination and/or treatment device constructed and operating in accordance with the invention.

FIG. 2 is a schematic illustration for explaining the updating in accordance with the invention, using a 3D ultrasound image dataset.

FIG. 3 is a schematic illustration for explaining the updating in accordance with the invention, using of a 2D ultrasound image.

DESCRIPTION OF THE PREFERRED EMBODIMENTS

In a schematic illustration, FIG. 1 shows an inventive examination and/or treatment device 1 having an ultrasound image acquisition device 2 as well as a control and processing device 3 that controls the operation of the ultrasound image acquisition device 2 and also undertakes the processing, editing and analysis of the image data. A set of 2D ultrasound images of an examination region—the heart of a patient 4 in this case—that are forwarded to the control and processing device 3, are acquired with the ultrasound device 2. In the illustrated example, the acquisition of the image data representing 2D ultrasound images ensues with triggering by an ECG 6 that is recorded in parallel, since the examination region 15 is a rhythmically moving organ, namely the heart. The ECG data are likewise forwarded to the control and processing device 3.

A position sensor 8 with which the spatial position of the ultrasound acquisition device 2, and thus the respective spatial position of each acquired 2D ultrasound image can be identified, is also provided at the ultrasound acquisition device 2. A suitable position detection system 16 is used for this purpose. The position data are likewise stored together with the 2D ultrasound images 5.

A preoperatively acquired 3D image dataset 7 of the examination region 15 is also present in the control and processing device 3. This can be a computed tomography dataset, a magnetic resonance dataset or a 3D angiography image dataset. Since this dataset was acquired preoperatively, i.e. at an arbitrary time before the current treatment, there is the possibility that it does not show the examination region in conformity with the current anatomical conditions. In order nonetheless to be able to employ this high-resolution 3D image dataset for producing a 3D reconstruction image in the context of a subsequent examination or treatment, it is necessary that it be updated, i.e. to adapt it to the current anatomical conditions.

The updating of the 3D image dataset can ensue in two ways. A first way is to directly employ the 2D ultrasound images 5, that are registered with a known spatial position with respect to the coordinate system of the 3D ultrasound image dataset. As an alternative, a 3D ultrasound image dataset 9 can be generated on the basis of the 2D ultrasound images 5 and utilized for the updating. This shall be discussed with reference to FIGS. 2 and 3.

A number of steps in accordance with the invention are schematically indicated as blocks in the control and processing device 3. After the 3D image dataset has been updated in step 10, the production of a 3D reconstruction image ensues in step 11. As illustrated by step 12 (only shown with broken lines), there is also the possibility of mixing an instrument introduced into the examination region 3 into this 3D reconstruction image. This can ensue using the 2D ultrasound images that may possibly show this instrument. Its position is detected; as a result of the registration of the 2D ultrasound images 5 relative to the 3D image dataset, and the detected position and orientation are mixed into the 3D volume image with accurate position and orientation. Of course, there is also the possibility of employing other two-dimensional images, for example X-ray fluoroscopic images, that show the instrument in the examination volume instead of the 2D ultrasound images. The 3D reconstruction image is subsequently presented at a monitor 13 with a representation of the instrument.

FIG. 2 shows the updating using a 3D ultrasound image dataset. This 3D ultrasound image dataset 9—like the 3D image dataset 7—is presented in the form of a volume. The respective volumes are subdivided into a number of small partial volumes, referred to as voxels. Four voxels 7a, 7b, 7c and 7d are shown in the 3D image dataset 7; four corresponding voxels 9a, 9b, 9c and 9d are shown in the 3D ultrasound image dataset 9. For the deformation and updating of the 3D image dataset 7, the individual voxels are compared to one another and a determination is made as to whether the voxels of the 3D image dataset 7 agree with the corresponding voxels of the 3D ultrasound image dataset 9. In the illustrated example, the voxels 7a, 7b, 7c and the voxels 9a, 9b, 9c coincide, i.e. there is an image data match. The voxel 7d, which has been selected merely as an example, cannot be mapped onto the voxel 9d with exact orientation and position. For the updating, a rigid registration of this voxel and of course of every other unmatched voxel, now ensues by translation and/or rotation of the respective voxel until it fits with the respective comparison voxel in the 3D ultrasound image dataset. The voxel 7d is translationally or rotationally modified until it can be mapped congruently onto the voxel 9d. A determination of the deformation of updating parameters ensues from this modification. When the corresponding deformation parameters have been identified for every non-matching voxel, then the actual updating of the 3D image dataset 7 ensues, i.e. it is modified dependent on the acquired updating requirements. The acquisition of differences, if any, within the voxels ensues by an analysis of the respective grayscale values.

FIG. 3 shows the updating using a 2D ultrasound image a schematic illustration. The 3D image dataset 7 also is shown in FIG. 3 in the form of a three-dimensional cube. A 2D ultrasound image 5 is then mixed into this 3D image dataset 7 with exact position and orientation. As described, the exact spatial position of the 2D ultrasound image 5 in the 3D volume is known because of the acquisition of the spatial lay of a 2D ultrasound image 5 using the position sensor 5 and due to the registration of the 2D ultrasound image 5 with the coordinate system of the 3D image dataset 7, so that this mixing can ensue. A check is also made, for example via a grayscale analysis, as to how the examination region that is shown in the tomogram plane of the 3D image dataset 7 and the examination region as shown in the 2D ultrasound image 5 coincide relative to one another. The tomogram plane from the 3D image dataset 7 is shown at the left in the illustrated example, the 2D ultrasound image 5 shown next to it, being mixed in over it or into it. The examination region is shown idealized as a circle in the 3D tomogram plane (at the left), whereas it is oval in the 2D ultrasound image that indicates the current anatomical conditions. The determination of the deformation or updating parameters now ensues such, for example via a suitable grayscale analysis or an edge detection algorithm, which describe how the presentation of the examination region shown in the 3D plane of section image 14 is to be shifted or deformed until it coincides with the presentation shown in the 2D ultrasound image 5. This mixing and determination of the deformation parameters ensues until an updating of the complete 3D image dataset 7 is possible.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for three-dimensional presentation of an examination region of a patient as a 3D reconstruction image, comprising the steps of:
    employing a preoperatively acquired 3D image dataset of an examination region of a subject that was acquired at a preoperative time preceding implementation of a medical procedure on the subject involving said examination region, said 3D image dataset representing voxels of said examination region;
    with an ultrasound system, acquiring a plurality of 2D image datasets respectively representing 2D ultrasound images of said examination region contemporaneously with said medical procedure involving said examination region;
    updating the preoperatively acquired 3D image dataset using said 2D image datasets representing said 2D ultrasound images to change some of said voxels of said 3D image dataset, to produce an updated 3D image dataset comprised of said preoperatively acquired 3D image dataset and the changed voxels, said updated 3D image dataset representing said examination region contemporaneously with said medical procedure; and
    reconstructing a 3D reconstruction image from said updated 3D image dataset and using said 3D reconstruction image in said medical procedure.

2. A method as claimed in claim 1 comprising employing a dataset selected from the group consisting of a computed tomography dataset, a magnetic resonance dataset, and an X-ray dataset, as said 3D image dataset.

3. A method as claimed in claim 1 wherein the step of updating said preoperatively acquired 3D image dataset using said 2D image datasets representing said 2D ultrasound images comprises updating said preoperatively acquired 3D image dataset directly from said 2D ultrasound images.

4. A method as claimed in claim 3 wherein the step of acquiring said 2D datasets representing said plurality of 2D datasets of the examination region comprises acquiring said plurality of 2D ultrasound images with an ultrasound applicator having a position sensor allowing identification of a spatial position and orientation of each of said plurality of 2D ultrasound images represented by said 2D datasets, and comprising the additional steps of:
    using said identification of the spatial position and orientation of each of said plurality of 2D ultrasound images, registering one of said plurality of 2D ultrasound images represented by one of said 2D image datasets relative to coordinates of said 3D image dataset so that the spatial position and orientation of said one of said plurality of 2D ultrasound images relative to said 3D image dataset is known;
    mixing said one of said 2D image datasets representing said one of said plurality of 2D images with exact position and orientation into a corresponding sectional plane image of said 3D image dataset; and
    deforming said sectional plane image of said 3D image dataset to conform to said one of 2D ultrasound images.

5. A method as claimed in claim 4 comprising the additional step of segmenting a surface of the examination region in said 3D image dataset before mixing one of said 2D image datasets representing said one of said 2D ultrasound images into said 3D image dataset.

6. A method as claimed in claim 1 wherein the step of updating said preoperatively acquired 3D image dataset using 2D image datasets representing said 2D ultrasound images comprises generating a 3D ultrasound image dataset from said 2D image datasets and updating said 3D image dataset using said 3D ultrasound image dataset.

7. A method as claimed in claim 6 comprising updating said 3D image dataset using said 3D ultrasound image dataset by overlaying said 3D image dataset and said 3D ultrasound image dataset, identifying dataset portions, as identified dataset portions, of said 3D image dataset that do not conform with corresponding dataset portions of said 3D ultrasound image dataset, and deforming said identified dataset portions of said 3D image dataset, by at least one of translation and rotation, until said identified portions of said 3D image dataset conform to said corresponding dataset portions of said 3D ultrasound image dataset.

8. A method as claimed in claim 7 wherein said 3D image dataset, as a result of said deformation, contains an irregularity selected from the group consisting of an overlap region and a gap region, and comprising the additional step of smoothing said irregularity by interpolation.

9. A method as claimed in claim 1 comprising the additional step of generating a 3D ultrasound image dataset from said 2D image datasets, and wherein the step of updating said preoperatively acquired 3D image dataset using said 2D image datasets representing said 2D ultrasound images comprises updating said preoperatively acquired 3D image dataset directly from said 3D ultrasound image dataset.

10. A method as claimed in claim 1 wherein said examination region is a moving region exhibiting a motion phase, and comprising the additional steps of:
    acquiring said motion phase; and
    employing only image data from said 3D image dataset acquired in a same motion phase as said 2D image datasets representing said 2D ultrasound images for updating said 3D image dataset to produce said updated 3D image dataset.

11. A method as claimed in claim 10 wherein said examination region is a heart, wherein the step of acquiring said motion phase comprises obtaining an ECG of said heart, and using said ECG to identify said same locations in said motion phase.

12. A method as claimed in claim 10 comprising the additional steps of:
    in addition to acquiring said motion phase, identifying respective points in time at which said 2D image datasets are acquired; and
    employing only image data from said 3D image dataset acquired at respective same points in time as said 2D image datasets for updating said 3D image dataset to produce said updated 3D image dataset.

13. A method as claimed in claim 12 wherein said examination region is a heart, and wherein the step of acquiring said motion phase comprises acquiring an ECG of the heart, and using said ECG to identify said same locations in said motion phase and said same points in time.

14. A method as claimed in claim 1 wherein the step of acquiring said plurality of 2D image datasets respectively representing said 2D ultrasound images comprises extracorporeally acquiring said 2D image datasets.

15. A method as claimed in claim 1 wherein the step of acquiring said plurality of 2D image datasets respectively representing said 2D ultrasound images comprises intracorporeally acquiring said 2D image datasets.

16. A method as claimed in claim 1 comprising, in said medical procedure, introducing an instrument into said examination region, and wherein the step of acquiring said plurality of 2D image datasets respectively representing said 2D ultrasound images comprises acquiring said plurality of 2D image datasets using an ultrasound applicator carried by said instrument, and comprising the additional steps of identifying a position of said instrument in said examination region from at least one of said 2D ultrasound images, and displaying said position of said instrument in said updated 3D reconstruction image.

17. An apparatus for three-dimensional presentation of an examination region of a patient as a 3D reconstruction image, comprising:
an image processor containing a 3D image dataset of an examination region of a subject that was acquired prior to conducting a medical procedure on the subject involving said examination region, said 3D image dataset representing voxels of said examination region;
an ultrasound image acquisition device that acquires a plurality of 2D image datasets respectively representing plurality of 2D ultrasound images of said examination region contemporaneously with said medical procedure;
said image processor supplied with said plurality of 2D image datasets representing said 2D ultrasound images that updates the preoperatively acquired 3D image dataset using said plurality of 2D image datasets representing said 2D ultrasound images to change some of said voxels of said 3D image dataset, to produce an updated 3D image dataset comprised of said preoperatively acquired 3D image dataset and the changed voxels, said updated 3D image dataset representing said examination region contemporaneously with said medical procedure, and reconstructing a 3D reconstruction image from said updated 3D image dataset; and
a monitor connected to said image processor for displaying said 3D reconstruction image during said medical procedure.

18. An apparatus as claimed in claim 17 wherein said image processor contains a dataset selected from the group consisting of a computed tomography dataset, a magnetic resonance dataset, and an X-ray dataset, as said 3D image dataset.

19. An apparatus as claimed in claim 17 wherein said image processor updates said preoperatively acquired 3D image dataset using said plurality of 2D image datasets respectively representing said 2D ultrasound images by updating said preoperatively acquired 3D image dataset directly from said 2D image datasets.

20. An apparatus as claimed in claim 19 wherein said ultrasound image acquisition device has a position sensor, and wherein said apparatus comprises a position detection system which detects a position of said position sensor and which generates an output identifying a spatial position and orientation of each of said plurality of 2D ultrasound images, and wherein said image processor is supplied with said output and uses said information identifying the spatial position and orientation of each of said plurality of 2D ultrasound images to register one of said plurality of 2D ultrasound images represented by one of said 2D datasets relative to coordinates of said 3D image dataset so that the spatial position and orientation of said one of said plurality of 2D ultrasound images relative to said 3D image dataset is known; and mixes said one of said plurality of 2D image datasets representing said one of said plurality of 2D images with exact position and orientation into a corresponding sectional plane image of said 3D image dataset, and deforms said sectional plane image of said 3D image dataset to conform to said 2D ultrasound image.

21. An apparatus as claimed in claim 20 wherein said image processor segments a surface of the examination region in said 3D image dataset before mixing said one of said 2D image datasets representing said one of said 2D ultrasound images into said 3D image dataset.

22. An apparatus as claimed in claim 17 wherein said image processor updates said preoperatively acquired 3D image dataset using said plurality of 2D image datasets representing said 2D ultrasound images by generating a 3D ultrasound image dataset from said 2D image datasets and updates said 3D image dataset using said 3D ultrasound image dataset.

23. An apparatus as claimed in claim 22 wherein said image processor updates said 3D image dataset using said 3D ultrasound image dataset by overlaying said 3D image dataset and said 3D ultrasound image dataset, and identifies dataset portions, as identified dataset portions, of said 3D image dataset that do not conform with corresponding dataset portions of said 3D ultrasound image dataset, and deforms said identified dataset portions of said 3D image dataset, by at least one of translation and rotation, until said identified portions of said 3D image dataset conform to said corresponding dataset portions of said 3D ultrasound image dataset.

24. An apparatus as claimed in claim 23 wherein said 3D image dataset, as a result of said deformation, contains an irregularity selected from the group consisting of an overlap region and a gap region, and wherein said image processor smoothes said irregularity by interpolation.

25. An apparatus as claimed in claim 17 wherein said image processor generates a 3D ultrasound image dataset from said plurality of datasets representing said 2D ultrasound images, and updates said preoperatively acquired 3D image dataset using said 2D image datasets by updating said preoperatively acquired 3D image dataset directly from said 3D ultrasound image dataset.

26. An apparatus as claimed in claim 17 wherein said examination region is a moving region exhibiting a motion phase, and comprising a unit for acquiring said motion phase, and wherein said image processor is supplied with motion phase and employs only image data from said 3D image dataset acquired in a same motion phase as said 2D image datasets representing 2D ultrasound images for updating said 3D image dataset to produce said updated 3D image dataset.

27. An apparatus as claimed in claim 26 wherein said examination region is a heart, wherein said unit for acquiring said motion phase obtains an ECG of said heart, and wherein said image processor uses said ECG as said motion phase to identify said same locations in said motion phase.

28. An apparatus as claimed in claim 26 comprising a unit for identifying respective points in time at which said 2D image datasets representing said 2D ultrasound images are acquired, and employs only image data from said 3D image dataset acquired at respective same points in time as said 2D image datasets for updating said 3D image dataset to produce said updated 3D image dataset.

29. An apparatus as claimed in claim 28 wherein said examination region is a heart, and wherein said unit for acquiring said motion phase obtains an ECG of the heart, and wherein said image processor uses said ECG to identify said same locations in said motion phase and said same points in time.

30. An apparatus as claimed in claim 17 wherein said ultrasound image acquisition device extracorporeally acquires plurality of 2D image datasets representing said 2D ultrasound images.

31. An apparatus as claimed in claim 17 wherein said ultrasound image acquisition device intracorporeally acquires plurality of 2D image datasets representing said 2D ultrasound images.

32. An apparatus as claimed in claim 17 comprising a medical instrument adapted, in said medical procedure, for introduction into said examination region, and wherein said ultrasound image acquisition device is an ultrasound applicator carried by said instrument, and wherein said image processor identifies a position of said instrument in said examination region from at least one of said 2D ultrasound images, and wherein said monitor displays said position of said instrument in said updated 3D reconstruction image at said monitor.

* * * * *